United States Patent [19]

Malinowski

[11] 3,946,241
[45] Mar. 23, 1976

[54] LIGHT DETECTOR WITH PULSED LIGHT SOURCE AND SYNCHRONOUS DATA GATING

[75] Inventor: William J. Malinowski, Pembroke, Mass.

[73] Assignee: Pyrotector, Incorporated, Hingham, Mass.

[22] Filed: Apr. 14, 1975

[21] Appl. No.: 568,015

Related U.S. Application Data

[63] Continuation-in-part of Ser. No. 419,206, Nov. 26, 1973, abandoned.

[52] U.S. Cl. ............ 250/574; 250/221; 340/237 S; 250/214 R
[51] Int. Cl.² ................................. G01N 21/26
[58] Field of Search ........... 250/554, 221, 222, 206, 250/574, 214 B, 214 RC; 340/237 R, 237 S, 258 B

[56] References Cited
UNITED STATES PATENTS

| | | | |
|---|---|---|---|
| 3,534,351 | 10/1970 | Harnden | 340/237 S |
| 3,563,661 | 2/1971 | Charlson | 250/574 |
| 3,710,365 | 1/1973 | Barnes | 340/237 S |
| 3,719,938 | 3/1973 | Perlman | 250/221 |
| 3,727,207 | 4/1973 | Missio | 340/258 B |
| 3,749,918 | 7/1973 | Jones | 340/258 B |

Primary Examiner—Archie R. Borchelt
Assistant Examiner—D. C. Nelms
Attorney, Agent, or Firm—Robert E. Ross

[57] ABSTRACT

A detector of the type utilizing photo-electric detection of reflected light which is almost completely immune to false alarms from changing ambient light and random electrical noise, with a sensitivity that is independent of ambient light, with a power consumption low enough to permit battery operation for a period of over 12 months. The light source is a light emitting diode which is pulsed at a low repetition rate, such as one pulse every two seconds, by an extremely short pulse, such as 20 microseconds. Voltage pulses generated when the reflected pulsed light is received by the photo-generative cell is amplified and applied to a level detector, the output of which is applied to the "set" terminal of a flip-flop circuit. The amplifier is on continuously, however the level detector is pulsed to the on condition simultaneously with the on pulse to the light emitting diode, and for the same period of time. Simultaneously with the application of the pulse to the light emitting diode and the level detector, a shorter pulse is applied to a bi-stable switching device such as to the 're-set' terminal of the flip-flop circuit. The output of the flip-flop circuit may be applied through an integrator to an alarm energizing switch. The integrator has a time constant that is longer than the pulse time, so that more than a single pulse from the flip-flop must be applied thereto to activate the alarm energizing switch. The photo-voltaic cell is capacitor coupled to the amplifier, so that constant or changing light, having a rate of change below that to which the amplifier responds, cannot affect the amplifier to cause a false alarm. Since the level detector is on only about 1/100,000 of the total time, a false alarm can be caused only by an extremely fast change in ambient light or a random noise pulse, that occurs at the exact instant the level detector is on, in two consecutive pulse times.

8 Claims, 4 Drawing Figures

U.S. Patent   March 23, 1976   3,946,241
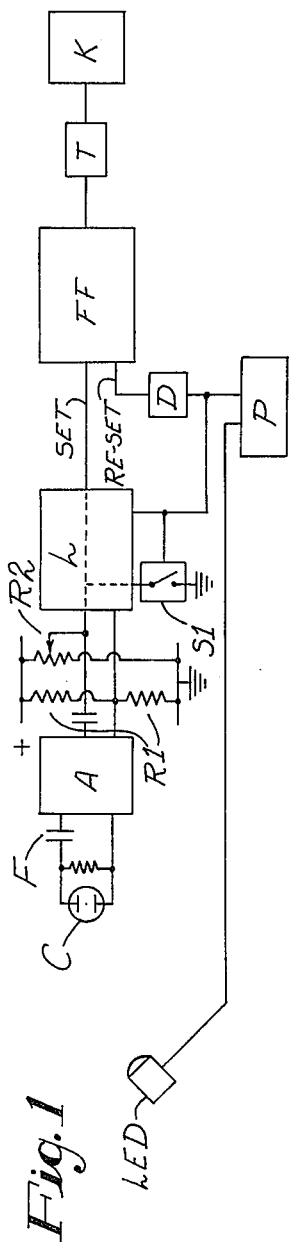
Fig. 1
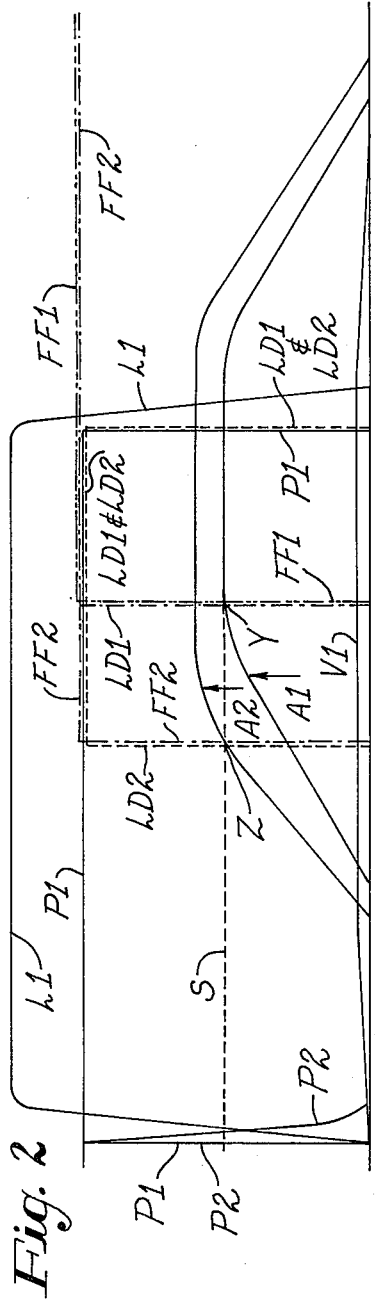
Fig. 2
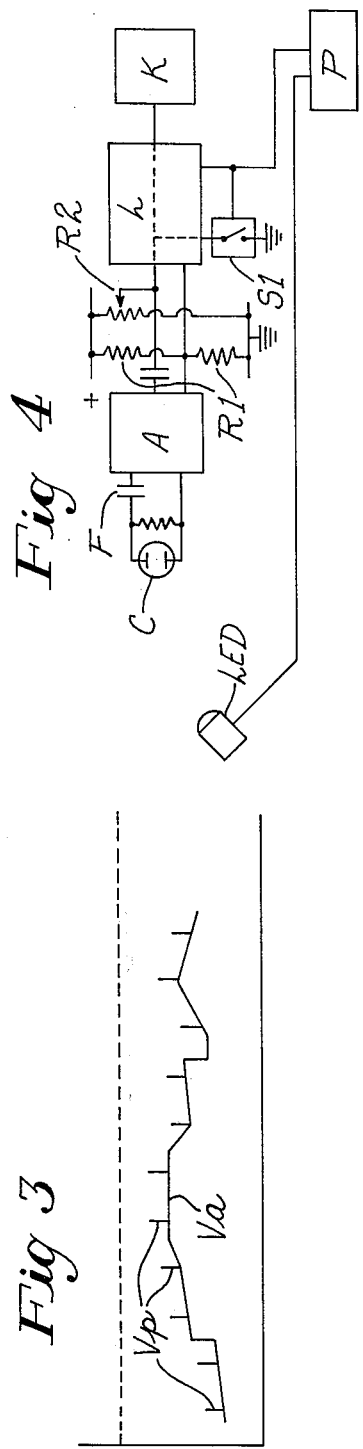
Fig. 4
Fig. 3

LIGHT DETECTOR WITH PULSED LIGHT SOURCE AND SYNCHRONOUS DATA GATING

This application is a continuation-in-part of application Ser. No. 419,206, filed Nov. 26, 1973, now abandoned.

BACKGROUND OF THE INVENTION

Many forms of smoke detectors are known that utilize the so-called Tyndall effect, in which light reflected from smoke particles is detected and the resulting signal amplified to actuate an alarm. Most commercial units utilize a continuously operating incandescent lamp as the light source. Such a detector that has achieved great commercial success is disclosed in U.S. Pat. No. 3,382,762 issued Jan. 25, 1966. Smoke detectors based on this principle have the disadvantage of high current consumption and susceptibility to false alarms due to changing levels of ambient light and changes in line voltage. Hence such devices must be enclosed in a housing that allows diffusion of air into the housing without allowing ambient light to enter, the electrical circuitry must provide means for compensating for changes in line voltage, and the photo-electric detectors must have a high degree of uniformity and stability. Meeting these requirements adds considerably to the cost of the device.

To avoid some of the above disadvantages it has been proposed to utilize a flashing light source, such as a gas filled tube, to reduce the current consumption. It has also been proposed to modulate the pulsed light at a predetermined frequency and provide an amplifier that responds only to said frequency. Such a system is illustrated in U.S. Pat. No. 3,316,410 issued Apr. 25, 1967. it has also been proposed that the means amplifying the signal from the light sensitive element should be operative only while the light source is on, so that ambient light changes or electrical distrubances that occur during the period the amplifier is off cannot cause a false alarm. However, in such a system, ambient light changes and electrical disturbances that occur while the amplifier is on can nevertheless cause a false alarm. Examples of ambient light changes that can affect a detector of this type are flashlights, strong sunlight, turning on of room lights, camera flash bulbs, and lightning. Hence the use of a pulsed light source and a pulsed amplifier as shown in the prior art, although having the advantage of lower power consumption, does little to reduce the possibility of false alarms, and hence to avoid false alarms from such causes the sensitivity of the device must be reduced.

SUMMARY OF THE INVENTION

The detector disclosed herein comprises a light emitting diode and a photo-generative cell positioned to receive light reflected from smoke or other substance in the path of the beam from the light emitting diode. The photo-generative cell is capacitor coupled to an A.C. amplifier, the output of which is fed to a level detector such as a differential comparator. The output of the level detector, which produces an output only when the input signal is above a predetermined value, is fed to an alarm actuating device. A bi-stable switching device, such as a flip-flop circuit, and a signal integrating device may be interposed between the output of the level detector and the input of the alarm actuating device.

A pulse generator is provided which provides periodic pulses simultaneously to the light-emitting diode to cause it to emit light to the level detector to turn it on, and provides, through a discriminating circuit, a short pulse to the bi-stable switching device to turn it off.

In a preferred embodiment of the device, the pulse has a duration of about 20 micro-seconds, and a repetition rate of once every 2 seconds. The amplifier is designed to accept only voltage pulses having a rise time corresponding to a frequency of between 1,000 and 100,000 cycles, so that the amplifier voltage pulse can reach its maximum value and achieve a constant value within the pulse time.

The amplifier may be continuously energized, however the level detector is energized only for the duration of the pulse. During the time between pulses, the level detector is turned off and the signal lead thereof is connected to ground, so that any signal through the amplifier due to random noise during the period that the level detector is off, passes to ground.

In one embodiment of the invention, to further reduce the possibility of an alarm from a continuous source of random noise, an integrating circuit is provided in the signal output circuit, having a time constant such that at least two consecutive pulses are required to allow a signal to pass from the integrator to the alarm activating device.

During each periodic pulse cycle, the light emitting diode is turned on, the level detector is turned on, and the bi-stable switching device is pulsed to the off condition at the beginning of the pulse. If smoke (or other substance) is present, light reflected therefrom onto the photo-generative cell causes a pulse of voltage to appear at the amplifier input. If the amplified pulse at the level detector is of sufficient magnitude to satisfy the requirements of the level detector, a signal pulse passes therefrom to the alarm actuating device.

In embodiments of the invention which have a bi-stable switching device such as a flip-flop, and an integrating device, the first signal pulse will be applied to the "set" terminal of the flip-flop and will be stored in the integrating device. At the beginning of the next periodic pulse, the short pulse to the re-set terminal of the flip-flop will turn the flip-flop output off; however, if smoke is still present, signal pulse generated by the reflected light pulse will again turn on the flip-flop and the second signal pulse will pass to the integrator, which will actuate the alarm.

Ordinary changes in ambient light cannot cause a false alarm, because the amplifier cannot respond to any voltage change at the input with a rate of change corresponding to a frequency of less than about 1,000 cycles, and such change would have to occur during the 20 micro-seconds that the pulse is being applied to the level detector. Similarly, random noise, to generate a signal at the amplifier input sufficient to produce an output high enough to pass through the level detector, would have to occur during the time the level detector is on, and would have to produce a signal at the amplifier input of the proper polarity.

BRIEF DESCRIPTION OF THE DRAWING

FIG. 1 is a schematic diagram of an electrical circuit for use in a smoke detector embodying the features of the invention;

FIG. 2 is a diagram illustrating the time spacing of the pulses applied to the light emitting diode and the level detector;

FIG. 3 is a diagram illustrating the voltage pulse appearing at the amplifier with 2% smoke in the view of the photo-generative cell at various ambient light levels.

FIG. 4 is a schematic diagram of a modified form of electrical circuit embodying the features of the invention.

DESCRIPTION OF THE ILLUSTRATED EMBODIMENT

Referring to FIG. 1, there is illustrated an electronic circuit for use in a smoke detector operating on the reflected light principle. The circuit includes a light emitting diode LED and a photo-voltaic cell C positioned out of the direct line of the beam of light from the light emitting diode. in a preferred embodiment of the invention the cell C is positioned to view a portion of the beam in front of the LED at an angle of about 135° from the axis of the beam, to take advantage of the well-known "forward scatter" effect.

The cell C is coupled through capacitor F to an amplifier A, the output of the amplifier being fed to the input of a level detector L, such as a differential comparator. The level detector output is fed to the "set" terminal of a flip-flop circuit FF, the output of which is fed to an alarm actuating device K.

In a preferred embodiment of the device, the differential comparator is normally off with the signal lead thereof clamped to ground by an electronic switch S1.

Light emitting diodes presently commercially available are rated, for example, for a maximum current of ½ ampere on a continuous basis, or for 10 amperes in pulses not to exceed 1 microsecond at 200 pulses per second. However, I have found that such diodes can be pulsed at 10 amperes for 20 micro-seconds, provided that the pulse repetition rate is much slower, for example 1 pulse every 1 or 2 seconds. As previously mentioned, this pulse duration allows the signal through the amplifier to reach a constant value within the pulse time, so that minor variations in pulse width will not affect this alarm point.

For this purpose and for others to appear hereinafter, a pulse generator P is provided, which provides a 20 micro-second pulse to the LED every 2 seconds, and also simultaneously applies a pulse to energize the level detector and to open switch S1. Hence the differential comparator is energized and its signal lead ungrounded only during the 20 micro-seconds out of each 2 seconds that the LED is energized.

Simultaneously with the application of the pulse to the LED and the level detector, a pulse is applied to the re-set terminal of the flip-flop circuit through a discriminator D, which converts said pulse to a spike of about 1 micro-second duration, occuring at the beginning of the pulse cycle.

The operation of the circuit can best be understood by reference to FIG. 2 of the drawing, which is a graph of the response of the various components of the circuit during one pulse. The horizontal scale represents time, and the vertical scale represents response. The vertical scale is arbitrary depending on the type of response, and the magnitude of the various curves on the vertical scale have no relation to each other except as described hereinafter.

Each cycle begins by the application of a pulse from the pulse generator to the LED, the level detector, and the flip-flop reset terminal. The pulse to the LED and the level detector are represented on the diagram by P1, since they are of the same duration. They may, of course, be of different magnitudes and different polarities. The pulse appearing at the re-set terminal of the flip-flop after passing through the discriminator is represented by P2. The application of the pulse to the LED produces a light output having a duration and relative intensity represented by curve L1.

If there is no smoke in the portion of the beam viewed by the cell C, there will be no pulse of voltage generated by the cell and hence no output from the amplifier. If the detector is subjected to varying ambient light, the cell will generate a varying D.C. voltage (see FIG. 3) which does not cause any amplifier response because of the capacitor coupling between the cell and the amplifier.

If there is smoke present in the pulsed light beam, a pulsed voltage signal will be produced by the cell, represented by curve VI of FIG. 2, which will be amplified by the amplifier to produce a signal at the input of the differential comparator, which signal will have a magnitude that is a function of the amount of smoke present. To avoid unnecessary alarms from acceptable amounts of smoke and dust in the atmosphere, the differential comparator is set to respond only to an amplifier output that corresponds to a predetermined smoke concentration. For example, in a preferred embodiment of the invention, the differential comparator is set to respond only if the smoke concentration is 2%, defined as the amount of smoke that absorbs 2% of a light beam 1 foot long. As illustrated in FIG. 2, the amplifier output level required to permit the output signal to pass through the differential is represented by the horizontal dashed line S.

In a particular embodiment of the invention the differential comparator may have a standby voltage difference between input terminals of about 100 millivolts, requiring a signal of over 100 millivolts from the amplifier to produce an output signal.

Means may also be provided at the level detector to adjust the standby voltage difference between terminals, to allow calibration of the system so that the alarm point will be at the desired 2%. In the present embodiment of the invention the calibration is accomplished by providing a voltage divider R1 across the power source, with the junction thereof connected to one of the inputs of the differential comparator, and providing a variable resistor R2 across the power supply with the center tap thereof connected to the other input.

If the amount of smoke in the view of the cell has reached the specified concentration, the amplifier output will be as shown in curve A1 reaching the line S at point Y, thereby producing a differential comparator output represented by line LD1, which applies a signal to the flip-flop set terminal, thereby turning on the flip-flop output (FF1 on FIG. 2) to energize the alarm.

At the end of the pulse to the LED and the differential comparator, both turn off so that the output from the differential comparator to the flip-flop is turned off. The flip-flop output, however, stays on until the beginning of the next pulse, at which time it is turned off by the pulse through the discriminator in the manner previously described.

As a greater concentration of smoke appears in the view of the cell, more reflected light is received by the cell, and the output voltage of the pulses applied to the amplifier increases, so that the amplifier output increases and reaches the required level S slightly sooner in the pulse cycle, as illustrated by curve A2, which reaches level S at point Z, thereby producing a differential comparator output represented by line LD2 and flip-flop output FF2.

Although the amplifier may continue to provide an output for a short time after the end of the pulse to the LED and the differential comparator, no output can exist after the end of the pulse, because the differential comparator is de-energized and the signal lead thereof clamped to ground by switch S1.

A smoke detector utilizing the above described circuit has a number of advantages over detectors of the prior art that have utilized a pulsing light source and a pulsed amplifier. By the use of a pulse of very short duration with a slow repetition rate, an amplifier with a response only to very high rates of change of input voltage, and the use of a pulsed level detector after the amplifier, the occurrence of false alarms due to changing light levels or due to electrical transients is almost completely eliminated.

A change of light level that could actuate the alarm must not only occur at an extremely high rate, but its occurrence must coincide with the time in which the level detector is on, which is only 1/100,000 of the total time.

For example, the turning on of an incandescent light cannot cause a false alarm, since the rate of rise of the light output from an incandescent bulb is much too slow to create a voltage pulse that can pass through the capacitor. Although the resulting increase in ambient light will increase the D.C. voltage at the cell terminals, subsequent pulses of light falling on the cell will cause the cell to generate an output voltage pulse on top of the D.C. voltage (assuming that the ambient light is not so strong as to saturate the cell) which will be detected by the amplfier.

This effect is illustrated in FIG. 3 where curve V$a$ represents the voltage at the cell due to ambient light level and V$p$ represents the cell voltage during the period that the LED is illuminated, with 2% smoke present. Since the response of the cell is substantially linear, the sensitivity of the device is not affected by changes in ambient light, since the pulse voltage at 2% smoke remains the same, regardless of the ambient light level, provided that the ambient light level is not so high as to cause saturation of the cell. In the curve of FIG. 3, the relative height of the ambient light voltage curve and the height of the voltage pulses are necessarily not in proportion, since the D.C. voltage from ambient light may be on the order of .1 volts whereas the additional voltage generated by the pulse of light reflected from smoke particles, at 2% smoke, is only about 600 microvolts.

Although certain light sources, such as lightning, some types of camera flash equipment, and welding apparatus may produce light with a rise time fast enough to be amplified and reach the level detector, such resulting signal not only must be great enough to satisfy the level detector requirements, but also must occur during the 20 micro-seconds that the level detector is on. The chance of a false alarm from such a source is therefore extremely remote.

In regard to possible false alarms from random electrical signals generated in the cell from radio transmitters, transients on the power supply line, and the like, not only must such signals occur at the proper instant, and generate a signal of adequate magnitude, the signal appearing at the amplifier input must be of the proper polarity.

In the illustrated embodiment of the invention, the signal from the flip-flop is led to an integrator T, comprising a resistor-capacitor networ, which integrates pulses received from the flip-flop to provide an output signal to the alarm energizing device K. In one embodiment, the integrator may have a time constant which is at least slightly greater than the total time between pulses, so that two pulses from the flip-flop are required to reach an output level from the integrator to actuate the alarm energizing device.

Although the use of the integrator may not be required in all installations in which the smoke detector is used, it has been found effective in preventing false alarms in locations that are near sources of continuous noise, such as might be produced by arcing electrical apparatus.

Fluorescent lights, which produce light pulses with a rapid rise time at a rate of 120 pulses per second could, over a period of time, produce two pulses so timed in relation to the detector pulse timing as to cause a false alarm. However, fluorescent lights produce light principally in a narrow frequency band, and this band can easily be kept from reaching the photo-voltaic cell by an optical filter.

Another major advantage of a smoke detector utilizing the circuit disclosed herein is its extremely low power consumption. Although the pulse to the LED may be of the order of 7 amperes, the short duration of the pulse, and the fact that the level detector is on only during the pulse permits a power consumption of the order of 300 micro-amperes at 6 volts. This power consumption is low enough to allow the device to be operated for over one year on battery power units small enough to be contained within a detector housing, with enough reserve power to energize a self-contained alarm.

Although the circuit of FIG. 1 was designed specifically for use in a smoke detector, the principles of the invention may be utilized in other types of detectors such as turbidity detectors, nephelometers, absorption photometers, proximity detectors, and detectors of the interrupted beam type. In some such applications it may be desirable that the alarm or other indication be energized by the first signal pulse, in which case the flip-flop FF and integrator T may be omitted, and a circuit as illustrated in FIG. 4 may be used.

In either case the circuit may also be modified to operate from a charge stored in a capacitor, as illustrated in my copending application Ser. No. 449,362 filed Mar. 8, 1974.

Since certain obvious changes may be made in the illustrated embodiments of the invention without departing from the scope thereof, it is intended that all matter contained herein be interpreted in an illustrative and not a limiting sense.

I claim:

1. In a detector of the type utilizing a pulsing light source and means for producing a signal pulse in response to the pulsed light under prdetermined conditions, the improvement comprising a level detector having an input connected to the output of the signal pulse producing means, said level detector producing an output signal only in response to an input signal pulse above a predetermined value, the output of the level detector being connected to an alarm actuating device, means rendering said level detector incapable of producing an output signal when the light source is de-denergized and rendering said level detector capable of producing an output signal only when the light source is emitting light.

2. A detector as set out in claim 1 in which a bi-stable switching device is connected between the level detector and the alarm actuating device, said bi-stable switching device being normally in a first condition in which the alarm actuating device is not actuated and is responsive to a pulse from the level detector to shift to a second condition in which the alarm actuating device is actuated, and means periodically returning the bi-stable switching device to the first condition.

3. A detector as set out in claim 2 in which means is provided for applying simultaneously a periodic pulse to the light source to cause it to emit light, to the level detector to render it capable of producing an output signal and to the bi-stable switching device, the periodic pulse to the bi-stable switching device being of substantially shorter duration than the periodic pulses to the light source and the level detector and being so applied to the bi-stable switching device as to insure that it is in the first condition during an initial portion of each periodic pulse to the light source and the level detector, whereby the occurrence of a signal pulse from the level detector to the bi-stable device in response to an input signal pulse will shift the bi-stable switching device to the second condition after the termination of the periodic pulse to the bi-stable device.

4. In a detector of the type utilizing a pulsing light source and means for producing a signal pulse in response to the pulsed light under predetermined conditions, the improvement comprising a level detector having an input connected to the output of the signal pulse producing means, said level detector producing an output signal only in response to an input signal pulse above a predetermined value, a flip-flop circuit having set and re-set terminals, the level detector output being connected to the set terminal of the flip-flop circuit, whereby the flip-flop output is turned on when the level detector produces an output signal, means periodically applying a signal to the re-set terminal of the flip-flop to turn off the flip-flop output, the output of the flip-flop being connected to an alarm actuatin unit, said level detector being rendered incapable of producing an output signal when the light source is de-energized and is rendered capable of producing an output signal only when the light source is emitting light.

5. A detector as set out in claim 4 in which the level detector is energized only when the light source is emitting light.

6. A detector as set out in claim 4 in which the signal lead of the level detector is connected to ground when the light source is de-energized so as to be incapable of producing an output signal to the flip-flop and said signal lead is disconnected from ground only during the time that the light source is emitting light.

7. In a detector of the type utilizing a pulsing light source and means for producing a signal pulse in response to the pulsed light under predetermined conditions, the improvement comprising a level detector having an input connected to the output of the signal pulse producing means, said level detector producing an output signal only in response to an input signal pulse above a predetermined value, a flip-flop circuit having set and re-set terminals, the level detector output being connected to the set terminal of the flip-flop circuit, whereby the flip-flop output is turned on when the level detector produces an output signal, the output of the flip-flop being connected to an alarm actuating unit, and a pulse generator for simultaneously applying a periodic pulse to the light source to cause said light source to emit light, to the level detector to render it capable of producing an output signal, and to the re-set terminal of the flip-flop to insure that the flip-flop output is off during an initial portion of each periodic pulse to the light source and the level detector, said periodic pulse to the flip-flop being of shorter duration than the pulse to the light source, whereby an output signal pulse from the level detector will turn on the flip-flop output.

8. A smoke detector of the type utilizing a pulsing light source and means for producing signal pulses in response to the pulsed light under certain condition and for utilizing signal pulses above a predetermined magnitude to actuate an alarm, said light source being a light emitting diode, said means for producing signal pulses being a photo-voltaic device capacitor coupled to an amplifier, said amplifier having a frequency response such that no appreciable output occurs below input frequencies below 1,000 cycles and a pulse generator applying individual pulses to the light emitting diode, said pulses having frequency components greater than about 1,000 cycles, a duration of about 20 micro-seconds and a repetition rate of between about 1 to 2 seconds, said means for utilizing the signal pulses to actuate an alarm having means requiring a signal pulse from at least two consecutive pulses to actuate the alarm.

* * * * *